United States Patent [19]
Li et al.

[11] Patent Number: 5,866,603
[45] Date of Patent: Feb. 2, 1999

[54] DERIVATIVES OF ESTRA 1,3,5(10)TRIENE-17-ONE, 3-AMINO COMPOUNDS AND THEIR USE

[75] Inventors: Pui-Kai Li, Library; Kyle W. Selcer, Export, both of Pa.

[73] Assignee: Duquesne University of the Holy Ghost, Pittsburgh, Pa.

[21] Appl. No.: 476,360

[22] Filed: Jun. 7, 1995

Related U.S. Application Data

[62] Division of Ser. No. 341,410, Nov. 17, 1994, Pat. No. 5,571,933.

[51] Int. Cl.$^6$ ..................................................... C07J 41/00
[52] U.S. Cl. .......................................... 514/303; 552/521
[58] Field of Search ............................................. 552/521

[56] References Cited

U.S. PATENT DOCUMENTS

| | | | |
|---|---|---|---|
| 3,325,481 | 6/1967 | Pappo | 260/239.5 |
| 3,383,384 | 5/1968 | Pappo | 260/239.5 |
| 3,449,327 | 6/1969 | Ruggieri et al. | 260/239.5 |
| 4,443,377 | 4/1984 | Van Rheenen | 260/397.4 |
| 4,444,767 | 4/1984 | Torelli et al. | 424/238 |
| 4,600,538 | 7/1986 | Walker | 260/397.45 |
| 5,571,933 | 11/1996 | Li et al. | 552/521 |

FOREIGN PATENT DOCUMENTS

| | | |
|---|---|---|
| 9113083 | 9/1991 | WIPO . |
| 9305064 | 3/1993 | WIPO . |

OTHER PUBLICATIONS

Vignon, F. et al., "Effects Of Plasma Estrogen Sulfates In Mammary Cancer Cells", *Endocrinology*, vol. 106, pp. 1079–1086 (1980).

(List continued on next page.)

*Primary Examiner*—Kimberly J. Prior
*Attorney, Agent, or Firm*—Diane R. Meyers; Arnold B. Silverman; Eckert Seamans Cherin & Mellott, LLC

[57] ABSTRACT

This invention discloses compounds useful as steroid sulfatase inhibitors. The compounds comprise the formula (1)

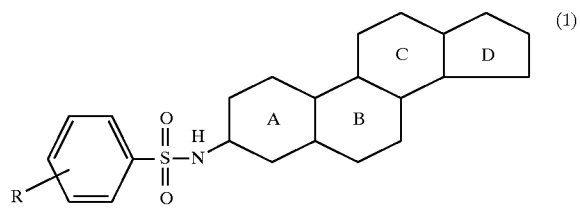

wherein (a) R is selected from the group consisting of hydrogen, a lower alkyl group, an alkoxy group, halogen, $NH_2$, $NO_2$, $C\equiv N$ and $N=C=S$; and (b) the ring system ABCD is a steroid nucleus selected from the group consisting of estrone, dehydroepiandrosterone, estradiols, estradiolesters, pregnenolone, substituted estrones, substituted dehydroepiandrosterones, substituted estradiols, substituted estradiolesters and substituted pregnenolone. The compounds also comprise the formula (5)

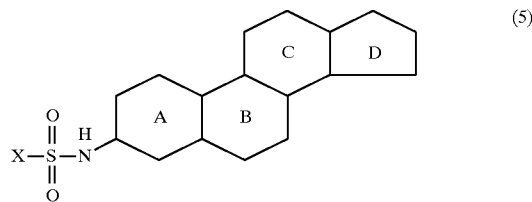

wherein (a) $R_1$ is hydrogen and $R_2$ is selected from the group consisting of $SO_2CF_3$, $SO_2NH_2$, $SO_2(C_1-C_6$-alkyl), $COCF_3$, $CONH_2$, $CO(C_1-C_6$-alkyl); and (b) the ring system ABCD is a steroid nucleus selected from the group consisting of estrone, dehydroepiandrosterone, estradiol, estradiolester, pregnenolone, substituted estrones, substituted dehydroepiandrosterone, substituted estradiols, substituted estradiolesters and substituted pregnenolone. The invention also discloses methods of treating a patient therapeutically and prophylactically for estrogen dependent diseases with the compounds of this invention.

40 Claims, 4 Drawing Sheets

OTHER PUBLICATIONS

Wilking, N. et al., "Oestrogen Receptors And Metabolism Of Oestrone Sulphate In Human Mammary Carcinoma", *Eur. J. Cancer*, vol. 16, pp. 1339–1344 (1980).

Bradlow, H.L., "A Reassessment Of The Role Of Breast Tumor Aromatization", *Cancer Research (Suppl.)*, vol. 42, pp. 3382s–3386s (1982).

Santner, S.J. et al., "In Situ Estrogen Production Via The Estrone Sulfatase Pathway In Breast Tumors: Relative Importance versus The Aromatase Pathway", *Journal of Clinical Endocrinology and Metabolism*, vo. 59, No. 1, pp. 29–33 (1984).

Santen, R.J. et al., "Enzymatic Control Of Estrogen Production In Human Breast Cancer: Relative Significance Of Aromatase versus Sulfatase Pathways", *Annals New York Academy Of Sciences*, vol. 464, pp. 126–137 (1986).

Pasqualini, J.R. et al., "Importance Of Estrogen Sulfates In Breast Cancer", *J. Steroid Biochem.*, vol. 34, Nos. 1–6, pp. 155–163 (1989).

Reed, M.J. et al., "Sulphatase Inhibitors: The Rationale For The Development Of A New Endocrine Therapy", *Reviews On Endocrine–Related Cancer*, vol. 45, pp. 51–62 (1993).

Howarth, N.M. et al., "Estrone Sulfamates: Potent Inhibitors Of Estrone Sulfatase With Therapeutic Potential", *J. Med. Chem.*, vol. 37, pp. 219–221 (1994).

DERIVATIVES OF ESTRA 1,3,5(10)TRIENE-17-ONE, 3-AMINO COMPOUNDS AND THEIR USE

This is a division of application Ser. No. 08/341,410, filed Nov. 17, 1994 now U.S. Pat. No. 5,571,933.

BACKGROUND OF THE INVENTION

1. Field of the Invention.

This invention relates to derivatives of estra 1,3,5(10) triene-17-one, 3-amino compounds. More specifically, it relates to compounds useful as steroid sulfatase inhibitors in estrogen dependent illnesses. Methods of employing these compounds for therapeutic and prophylactic treatment are also provided.

2. Background Information.

It is estimated that approximately 30–40% of all breast cancers are estrogen dependent. In post-menopausal advanced breast cancer patients, the estrogen levels are in order of magnitude higher than in plasma. However, H. L. Bradlow in "A Reassessment of the Role of Breast Tumor Aromatization," *Cancer Research,* Volume 42, pp. 3382–33865 (1982), detected no active uptake of estrogens by breast tumors, and he also pointed out that the circulating level of estrogen in post-menopausal women would not be sufficient to stimulate tumor growth.

Two pathways are proposed to occur in breast cancer cells to explain the high concentration of estrogens in breast tumors: (1) conversion of androstenedione to estrone by aromatase (aromatose pathway) and (2) conversion of estrone sulfate to estrone by estrone sulfatase (sulfatase pathway). This is disclosed by S. J. Santner, et al. in "In Situ Estrogen Production Via The Estrone Sulfatase Pathway in Breast Tumors: Relative Importance Versus the Aromatose Pathway." *J. Clin. Endocrinal Metab.,* Volume 59, pp. 29–33 (1984) and R. J. Santen, et al. in "Enzymatic Control of Estrogen production in Human Breast Cancer: Relative Significance of Aromatose Versus Sulfatase Pathways." *Ann NY Acad. Sci.,* Volume 464, pp. 126–137 (1986).

Recently more attention has been directed toward the sulfatase pathway. Estrone sulfate is the most abundant circulating estrogen in women and estrone sulfatase has been consistently found in human breast cancer cells. It was reported that a high percentage of [$^3$H] estrone sulfate was converted to estradiol in different hormone-dependent mammary cancer cell lines [MCF-7, R-27, T-47D] but little or no conversion was found in the hormone-independent mammary cancer cell lines (MDA-MB-231, MDA-MB-436). This is disclosed in F. Vignon, et al., "Effect of Plasma Estrogen Sulfate in Mammary Cancer Cells," *Endocrinology,* Volume 106, pp. 1079–1086 (1980) and J. R. Pasqualini, et al., "Importance of Estrogen Sulfates in Breast Cancer," *J. Steroid Biochem,* Volume 34, pp. 155–163 (1989). In addition, the conversion of [$^3$H] estrone sulfate to [$^3$H] estrone and [$^3$H] estradiol was also demonstrated by incubating the homogenates of mammary carcinoma tissue in vitro in 23 breast cancer patients and described by N. Wilking, et al. in "Oestrogen Receptors and Metabolism of Oestrone Sulphate in Human Mammary Carcinoma", *Eur J. Cancer,* Volume 16, pp. 1339–1344 (1980).

Santen, et al., supra, evaluated estrogen production from breast tumor by way of the estrone sulfate to estrone (sulfatase) pathway and compared it with the androstenedione to estrone (aromatose) pathway. When comparing the sulfatase with aromatase activity in human tumors at physiological levels of substrates, the amount of estrone produced through sulfatase was 10 times higher than through the aromatase pathway (2.8 pmol estrone/g protein verses 0.27 pmol/g protein) in human breast tumors. This suggested that the sulfatase pathway is significant and perhaps the primary means of local estrogen production in breast tumor tissues.

Preliminary results indicated the importance of estrone sulfate as a potential source of estrogen to support the growth of estrogen-dependent breast cancer. Potent inhibitors of estrone sulfatase may be potential therapeutic agents for the treatment of estrogen-dependent breast cancer. This was disclosed by Reed and co-workers in PCT/GB 92/01386 published as WO93/05063 and PCT/GB91/00270 published as WO91/13083.

Several groups of compounds have been reported to be estrone sulfatase inhibitors. M. J. Reed, et al. disclosed in "Sulphatase Inhibitors: The Rationale For The Development of a New Endocrine Therapy," *Reviews on Endocrine-Related Cancer,* Volume 45, pp. 51–62 (1993), the sulfatase inhibitory activities of estrone-3-0-methylthiophosphonates, estrone 3-0 alkyl and aryl sulfonates, estrone-3-0-phosphates and thiophosphonates and estrone sulfamates on MCF-7 cells and in human placental microsomes and breast tumor preparations. In "Estrone Sulfamates: Potent Inhibitors of Estrone Sulfatase With Therapeutic Potential," *J. Med. Chem.,* Volume 37, pp. 219–221 (1994), Nicola M. Howarth, et al. disclosed that estrone 3-0-sulfamates represent a new class of sulfatase inhibitor and are considerably more potent in MCF-7 breast cancer cells than estrone 3-0 methylthiophosphonate.

In spite of the prior art disclosure there remains a very real and substantial need for an inhibitor of estrogen sulfatase that is more metabolically stable, more active and more selective than known compounds having antitumor activity or as synergistic agents with antiestrogen compounds and aromatase inhibitors and for methods of using such compounds.

SUMMARY OF THE INVENTION

The present invention has met the hereinbefore described need. The present invention provides compounds comprising the formula (1)

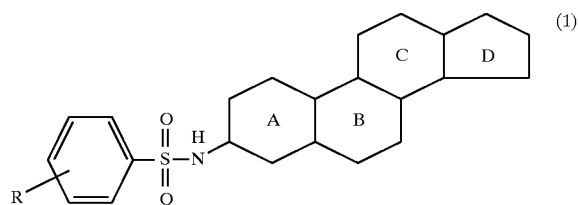

wherein (a) R is selected from the group consisting of hydrogen, a lower alkyl group, an alkoxy group, halogen, $NH_2$, $NO_2$, C≡N, N=C=S and (b) the ring system ABCD is a steroid nucleus selected from the group consisting of estrone, dehydroepiandrosterone, estradiols, estradiolesters, pregnenolone, substituted estrones, substituted dehydroepiandrosterones, substituted estradiols, substituted estradiolesters and substituted pregnenolone.

Preferably R is hydrogen, 4-methyl, 4-methoxy, a nitro selected from the group consisting of 2-$NO_2$, 3-$NO_2$, and 4-$NO_2$, a halogen selected from the group consisting of 4-F, 4-Cl, 4-Br and 4-I, an amine selected from the group consisting of 2-$NH_2$, 3-$NH_2$ and 4-$NH_2$, a cyano selected from the group consisting of 2-C≡N, 3-C≡N and 4-C≡N, and a isothiocyanate selected from the group consisting of 2-N=C=S, 3-N=C=S and 4-N=C=S. The most preferred R is to 2-$NH_2$.

In the above structure (1), the steroid ring system is preferably estrone, dehydroepiandrosterone or pregnenolone. Other suitable steroid ring systems are:

Substituted estrones, as follows:
  2-OH-estrone
  2-methoxy-estrone
  4-OH-estrone
  6 alpha-OH-estrone
  7 alpha-OH-estrone
  16 alpha-OH-estrone
  16 beta-OH-estrone Estradiols and substituted estradiols, as follows:
  2-OH-17 beta-estradiol
  2-methoxy-17 beta-estradiol
  4-OH-17 beta-estradiol
  6 alpha-OH-17 beta-estradiol
  7 alpha-OH-17 beta-estradiol
  16 alpha-OH-17 beta-estradiol
  16 beta-OH-17 alpha-estradiol
  16 beta-OH-17 beta-estradiol
  17 alpha-estradiol
  17 beta-estradiol
  17 alpha-ethinyl-17 beta-estradiol Estradiolesters and substituted estradiolesters, for example:
  17-beta-OH-methyl estradiol ester
  17-beta-OH-ethyl estradiol ester
  17-beta-OH propyl-estradiol ester
  17-beta-OH-butyl estradiol ester
  17-beta-OH-penthyl-estradiol ester
  17-beta-OH-hexyl-estradiol ester Substituted dehydroepiandrosterones, for example:
  6 alpha-OH-dehydroepiandrosterone
  7 alpha-OH-dehydroepiandrosterone
  16 alpha-OH-dehydroepiandrosterone
  16 beta-OH-dehydroepiandrosterone Pregnenolone and substituted pregnenolone, for example:
  6 alpha-OH-pregnenolone
  7 alpha-OH-pregnenolone
  16 alpha-OH-pregnenolone
  16 beta-OH-pregnenolone The first species of formula (1) is compounds comprising formula (2)

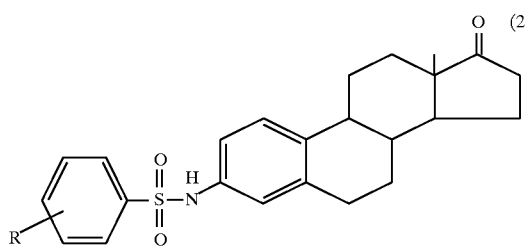

wherein R is selected from the group consisting of hydrogen, a lower alkyl group of one to six carbon atoms, an alkoxy group of one to four carbon atoms, $NH_2$, $NO_2$, $C{\equiv}N$, $N{=}C{=}S$ and a halogen selected from the group consisting of F, Cl, Br and I.

The second species of formula (1) is compounds comprising formula (3)

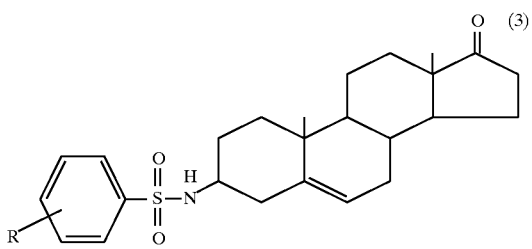

wherein R is selected from the group consisting of hydrogen, a lower alkyl group of one to six carbon atoms, an alkoxy group of one to four carbon atoms, $NH_2$, $NO_2$, $C{\equiv}N$, $N{=}C{=}S$ and a halogen selected from the group consisting of F, Cl, Br and I.

The third species of formula (1) is compounds comprising formula (4)

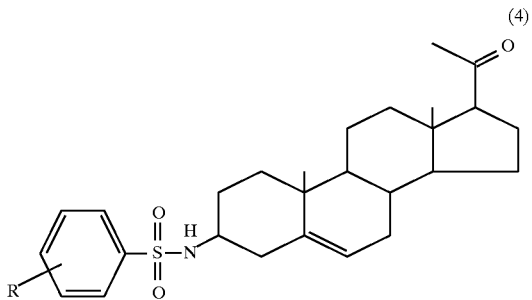

wherein R is selected from the group consisting of hydrogen, a lower alkyl group of one to six carbon atoms, an alkoxy group of one to four carbon atoms, $NH_2$, $NO_2$, $C{\equiv}N$, $N{=}C{=}S$ and a halogen selected from the group consisting of F, Cl, Br and I.

The present invention also provides compounds comprising formula (5)

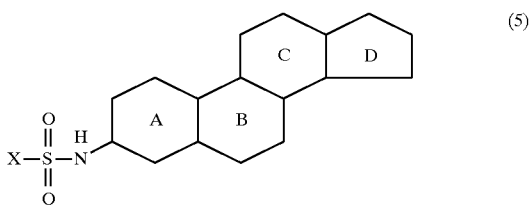

wherein (a) $R_1$ is hydrogen and $R_2$ is selected from the group consisting of $SO_2CF_3$, $SO_2NH_2$, $SO_2(C_1{-}C_6\text{-alkyl})$, $COCF_3$, $CONH_2$, $CO(C_1{-}C_6\text{-alkyl})$, and (b) the ring system ABCD is a steroid nucleus selected from the group consisting of estrone, dehydroepiandrosterone, estradiols, estradiolesters, pregnenolone, substituted estrones, substituted dehydroepiandrosterones, substituted estradiols, substituted estradiolesters and substituted pregnenolone. Preferably $R_1$ is hydrogen and $R_2$ is methyl ($CH_3$). Most preferably, $R_1$ and $R_2$ are hydrogen (H). In the above structure (5), the steroid ring system is preferably estrone, dehydroepiandrosterone or pregnenolone.

A species of the structure shown in formula (5) is the compounds comprising the formula (6)

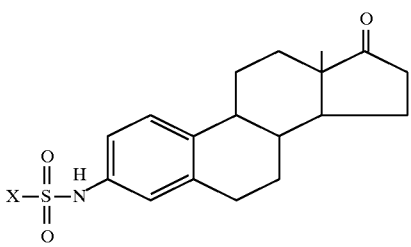

(6)

wherein $R_1$ is selected from the group consisting of hydrogen and $R_2$ is selected from the group consisting of $SO_2CF_3$, $SO_2NH_2$, $SO_2(C_1-C_6\text{-alkyl})$, $COCF_3$, $CONH_2$, $CO(C_1-C_6\text{-alkyl})$ A species of the structure shown in formula (5) is the compounds comprising the formula (7)

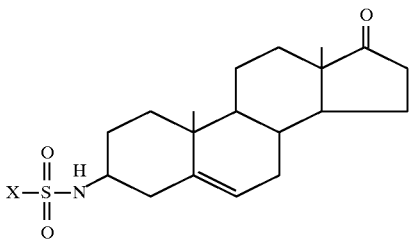

(7)

wherein $R_1$ is hydrogen and $R_2$ is selected from the group consisting of $SO_2CF_3$, $SO_2NH_2$, $SO_2(C_1-C_6\text{-alkyl})$, $COCF_3$, $CONH_2$, $CO(C_1-C_6\text{-alkyl})$.

A species of the structure shown in formula (5) is the compounds comprising the formula (8)

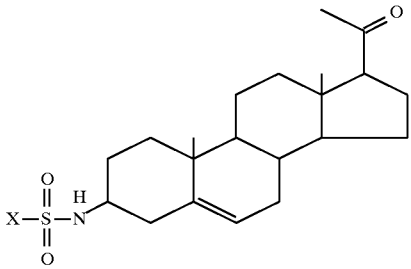

(8)

wherein $R_1$ is hydrogen and $R_2$ is selected from the group consisting of $SO_2CF_3$, $SO_2NH_2$, $SO_2(C_1-C_6\text{-alkyl})$, $COCF_3$, $CONH_2$, $CO(C_1-C_6\text{-alkyl})$.

This invention provides a process of using the derivatives of estra 1,3,5(10)triene-17-one, 3 amino compounds of formulas 1–8 described herein for therapeutic and prophylactic purposes including employing these compounds as antitumor agents and as synergistic agents with compounds such as anti-estrogen compounds and aromatase inhibitors. Derivatives of estra 1,3,5(10)triene-17-one, 3 amino compounds of this invention substantially inhibit steroid sulfatase compounds. This invention provides a process of using the derivatives of estra 1,3,5(10)triene-17-one, 3 amino compounds for therapeutic and prophylactic purposes as antitumor and synergistic agents against estrogen related illnesses selected from the group consisting of breast cancer, endometrial cancer, vaginal cancer, ovarian cancer and endometriosis.

It is an object of this invention to provide derivatives of estra 1,3,5(10)triene-17-one, 3 amino compounds for substantially inhibiting the steroid sulfatase enzyme produced in the body.

It is an object of this invention to provide derivatives of estra 1,3,5(10)triene-17-one, 3 amino compounds having antitumor or synergistic activity with anti-estrogen compounds and aromatase inhibitors.

It is a further object of this invention to provide derivatives of estra 1,3,5(10)triene-17-one, 3 amino compounds providing effective activity against estrogen dependent diseases such as, for example, breast cancer, ovarian cancer, vaginal cancer, endometrial cancer and endometriosis.

It is a further object of this invention to provide a method of using in a patient a therapeutically effective dosage of estra 1,3,5(10)triene-17-one, 3 amino compounds.

It is another object of this invention to provide a method of using in a patient a prophylactically effective dosage of estra 1,3,5(10)triene-17-one, 3 amino compounds as an estrogen depleting compound for women at risk.

It is yet another object of this invention to provide derivatives of estra 1,3,5(10)triene-17-one, 3 amino that are not metabolized to compounds that are estrogenic.

These and other objects of the invention will be more fully understood from the following description of the invention and the claims appended hereto.

DESCRIPTION OF THE PREFERRED EMBODIMENT

Figure 1:
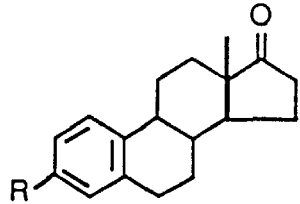
FIG. 1 discloses inhibition of estrone sulfatase activity by substituted phenyl-sulfonyl-amino estra 1,3,5(10)-triene-17-one in human placental microsome.

As used herein, the term "patient" means members of the animal kingdom, including, but not limited to, human beings.

Estrogen levels in breast tumors of post-menopausal women are as much as ten times higher than estrogen levels in plasma. The high level of estrogen in these tumors is postulated to be due to in situ formation of estrogen. Estrone sulfate is the most abundant circulating estrogen in women, and the enzyme estrone sulfatase has been shown to be present in breast cancer cells. Furthermore, estrone sulfate has been shown to stimulate growth of nitrosomethyl urea-induced tumor cells in castrated rats. Thus, inhibitors of estrone sulfatase may be potential agents for treatment of estrogen-dependent breast cancer.

Sulfaconjugated steroids are bound with considerably higher affinity by the human sterylsulfatase, (estrone sulfatase) than are unconjugated steroids. The search for an effective steryl sulfatase inhibitor has focused on synthetic analogs of steryl sulfates, especially estrone sulfate. Recently, we did a series of kinetic experiments have been undertaken to test the inhibitory potencies towards the human placental steryl-sulfatase of several analogs carrying different sulfamyl groups at position 3 of an invariable 3-desoxy-estrone moiety. From these experiments, we postulated that an oxygen atom or an uncharged but high electronegative substituent or at least a sterically or electronically similar link between the steroid ring and the sulfate moiety, is essential for high affinity binding towards the sulfatase. As a result, the following steryl, estra-1,3,5 (10)triene-17-one, 3-amino derivatives were synthesized as estrone sulfatase inhibitors.

The compounds comprise formula (1)

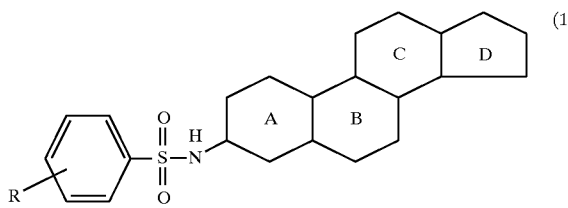

wherein (a) R is selected from the group consisting of hydrogen, a lower alkyl group, an alkoxy group, halogen, $NH_2$, $NO_2$ $C{\equiv}N$, $N{=}C{=}S$ and (b) the ring system ABCD is a steroid nucleus selected from the group consisting of estrone, dehydroepiandrosterone, estradiols, estradiolesters, pregnenolone, substituted estrones, substituted dehydroepiandrosterones, substituted estradiols, substituted estradiolesters and substituted pregnenolone. The lower alkyl group has one to six carbon atoms, the alkoxy group has one to four carbon atoms and the halogen is selected from the group consisting of fluorine, chlorine, bromine and iodine.

Preferably R is hydrogen, 4-methyl, 4-methoxy, a nitrate selected from the group consisting of 2-$NO_2$, 3-$NO_2$, and 4-$NO_2$, a halogen selected from the group consisting of 4-F, 4-Cl, 4-Br and 4-I, an amine selected from the group consisting of 2-$NH_2$, 3-$NH_2$ and 4-$NH_2$, a cyano selected from the group consisting of 2-$C{\equiv}N$, 3-$C{\equiv}N$, 4-$C{\equiv}N$, and a isothiocyanate selected from the group consisting of 2-$N{=}C{=}S$, 3-$N{=}C{=}S$, 4-$N{=}C{=}S$. The most preferable R is 2-$NH_2$.

In the above structure (1), the steroid ring system is preferably estrone, dehydroepiandrosterone, or pregnenolone. Other suitable ring systems are:
Substituted estrones, as follows:
   2-OH-estrone
   2-methoxy-estrone
   4-OH-estrone
   6 alpha-OH-estrone
   7 alpha-OH-estrone
   16 alpha-OH-estrone
   16 beta-OH-estrone
Estradiols and substituted estadiols, as follows:
   2-OH-17 betaestradiol
   2-methoxy-17 beta-estradiol
   4-OH-17 betaestradiol
   6 alpha-OH-17 beta-estradiol
   7 alpha-OH-17 beta-estradiol
   16 alpha-OH-17 beta-estradiol
   16 beta-OH-17 alpha-estradiol
   16 beta-OH-17 beta-estradiol
   17 alphaestradiol
   17 beta-estradiol
   17 alpha-ethinyl-17 beta-estradiol
Estradiolesters and substituted estradiolesters, for example:
   17-beta-OH-methyl estradiol ester
   17-beta-OH-ethyl estradiol ester
   17-beta-OH propyl-estradiol ester
   17-beta-OH-butyl estradiol ester
   17-beta-OH-penthyl-estradiol ester
   17-beta-OH-hexyl-estradiol ester Substituted dehydroepiandrosterones, for example:
   6 alpha-OH-dehydroepiandrosterone
   7 alpha-OH-dehydroepiandrosterone
   16 alpha-OH-dehydroepiandrosterone
   16 beta-OH-dehydroepiandrosterone
Pregnenolone and substituted pregnenolone, for example:
   6 alpha-OH-pregnenolone
   7 alpha-OH-pregnenolone
   16 alpha-OH-pregnenolone
   16 beta-OH-pregnenolone A first species of formula (1) is the compounds comprising formula (2)

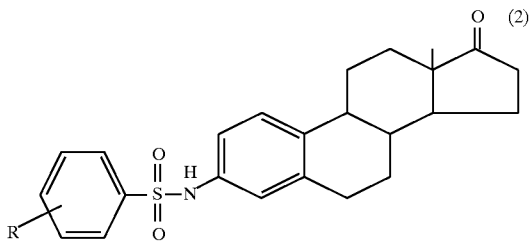

wherein R is selected from the group consisting of hydrogen, a lower alkyl group of one to six carbon atoms, an alkoxy group of one to four carbon atoms, $NH_2$, $NO_2$, $C{\equiv}N$, $N{=}C{=}S$ and a halogen selected from the group consisting of F, Cl, Br and I. Preferably R is hydrogen, 4-methyl, 4-methoxy, a nitro selected from the group consisting of 2-$NO_2$, 3-$NO_2$ and 4-$NO_2$, a halogen selected from the group consisting of 4-F, 4-Cl, 4-Br and 4-I, an amine selected from the group consisting of 2-$NH_2$ and 3-$NH_2$ and 4-$NH_3$, a cyano selected from the group consisting of 2-$C{\equiv}N$, 3-$C{\equiv}N$, 4-$C{\equiv}N$ and a isothiocyanate selected from the group consisting of 2-$N{=}C{=}S$, 3-$N{=}C{=}S$ and 4-$N{=}C{=}S$. The most preferred R is 2-$NH_2$.

A second species of formula (1) is the compounds comprising formula (3)

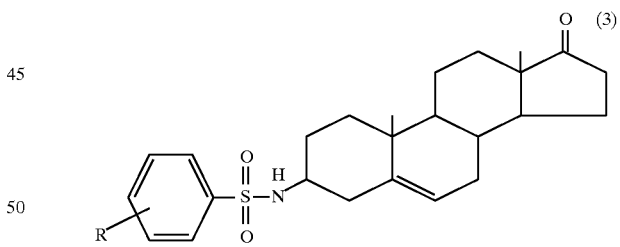

wherein R is selected from the group consisting of hydrogen, a lower alkyl group of one to six carbon atoms, an alkoxy group of one to four carbon atoms, $NH_2$, $NO_2$, $C{\equiv}N$, $N{=}C{=}S$ and a halogen selected from the group consisting of F, Cl, Br and I. Preferably R is hydrogen, 4-methyl, 4-methoxy, a nitrite selected from the group consisting of 2-$NO_2$, 3-$NO_2$ and 4-$NO_2$, a halogen selected from the group consisting of 4-F, 4-Cl, 4-Br and 4-I and an amine selected from the group consisting of 2-$NH_2$ and 3-$NH_2$ and 4-$NH_2$, a cyano selected from the group consisting of 2-$C{\equiv}N$, 3-$C{\equiv}N$ and 4-$C{\equiv}N$ and a isothiocyanate selected from the group consisting of 2-$N{=}C{=}S$, 3-$N{=}C{=}S$ and 4-$N{=}C{=}S$. The most preferred R is 2-$NH_2$.

A third species of formula (1) is the compounds comprising formula (4)

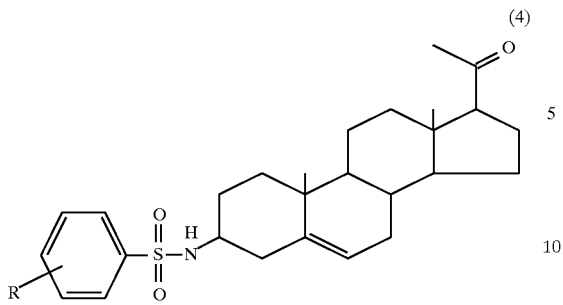

(4)

wherein R is selected from the group consisting of hydrogen, a lower alkyl group of one to six carbon atoms, an alkoxy group of one to four carbon atoms, $NH_2$, $NO_2$, $C\equiv N$ and $N=C=S$ and a halogen selected from the group consisting of F, Cl, Br and I. Preferably R is hydrogen, 4-methyl, 4-methoxy, a nitrite selected from the group consisting of $2-NO_2$, $3-NO_2$ and $4-NO_2$, a halogen selected from the group consisting of 4-F, 4-Cl, 4-Br and 4-I, an amine selected from the group consisting of $2-NH_2$ and $3-NH_2$, a cyano selected from the group consisting of $2-C\equiv N$, $3-C\equiv N$ and $4-C\equiv N$ and a isothiocyanate selected from the group consisting of $2-N=C=S$, $3-N=C=S$ and $4-N=C=S$.

The present invention also provides compounds comprising formula (5)

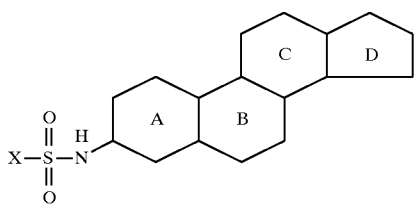

(5)

wherein (a) $R_1$ is hydrogen and $R_2$ is selected from the group consisting of $SO_2CF_3$, $SO_2NH_2$, $SO_2(C_1-C_6\text{-alkyl})$, $CONH_2$, $COCF_3$, $CO(C_1-C_6\text{-alkyl})$, and (b) the ring system ABCD is a steroid nucleus selected from the group consisting of estrone, dehydroepiandrosterone, estradiols, estradiolesters, pregnenolone, substituted estrones, substituted dehydroepiandrosterones, substituted estradiols, substituted estradiolesters and substituted pregnenolone. Preferably $R_1$ is hydrogen, and $R_2$ is methyl. Most preferably, $R_1$ and $R_2$ are hydrogen. In the above structure (5) the steroid ring system is preferably estrone, dehydroepiandrosterone or pregnenolone.

A species of the structure shown in formula (5) is the compounds comprising formula (6)

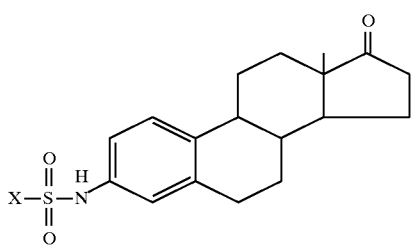

(6)

wherein $R_1$ is hydrogen and $R_2$ is selected from the group consisting of $SO_2CF_3$, $SO_2NH_2$, $SO_2(C_1-C_6\text{-alkyl})$ $CONH_2$, $COCF_3$, $CO(C_1-C_6\text{-alkyl})$.

A species of the structure shown in formula (5) is the compounds comprising formula (7)

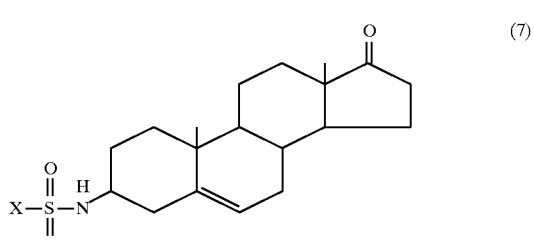

(7)

wherein $R_1$ is hydrogen and $R_2$ is selected from the group consisting of $SO_2CF_3$, $SO_2NH_2$, $SO_2(C_1-C_6\text{-alkyl})$ $CONH_2$, $COCF_3$, $CO(C_1-C_6\text{-alkyl})$.

A species of the structure shown in formula (5) is the compounds comprising formula (8)

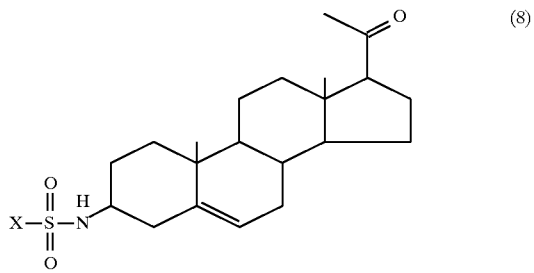

(8)

wherein $R_1$ is hydrogen and $R_2$ is selected from the group consisting of $SO_2CF_3$, $SO_2NH_2$, $SO_2(C_1-C_6\text{-alkyl})$ $CONH_2$, $COCF_3$, $CO(C_1-C_6\text{-alkyl})$.

In this invention the method of therapeutically treating a patient comprises providing a compound of formulas 1–8 given hereinabove, incorporating the compounds in a suitable pharmaceutical carrier, administering a therapeutically effective dosage of the compound incorporated in the carrier to a patient, and employing the method in therapeutically treating a patient for vaginal cancer, endometrial cancer, ovarian cancer and endometriosis.

The method also includes prophylactically treating a patient comprising providing a compound of formulas 1–8, incorporating the compounds in a suitable pharmaceutical carrier, administering a prophylactically effective dosage of the compounds incorporated in the carrier to a patient and employing the method in prophylactically treating a patient at risk with a estrogen depleting compound to provide protection against estrogen related diseases.

Examples of suitable pharmaceutical carriers are physiologic saline (0.9% sodium chloride) or 5% dextrose in water.

The compounds of this invention incorporated into the pharmaceutical carrier may be administered to a patient by parenteral injection, such as for example, intravenously, intrathecally, intramuscularly or intra-arterially. Other potential routes of administration include, for example, orally, transdermally or by other means. The dosage of, route of, administration of and duration of therapy with the compounds of this invention, which can readily be determined by those skilled in the art, will be individualized according to the illness being treated, body weight of the patient, other therapy employed in conjunction with the compounds of this invention and the condition, clinical response and tolerance of the patient.

The following are examples of how a preferred compound is prepared and employed in the present invention:

EXAMPLE I

The synthesis of 3 [(3-nitrophenylsulfonyl)-amino] estra-1,3,5(10)triene-17-one was as follows:

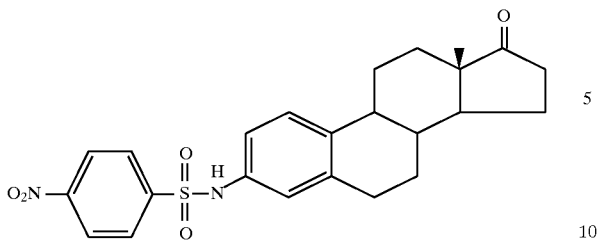

3-Nitrophenylsulfonyl chloride (1.65 g, 7.4 mmol) was added in one portion to a stirred solution of estra-1,3,5(10)-triene-17-one, 3-amine ($E_1$-$NH_2$) (1 g, 3.7 mmol) in anhydrous (25 ml) at 0° C. The reaction mixture was allowed to warm to room temperature and stirring continued for 24 hours. The reaction mixture was poured onto ice and the resulting aqueous solution was extracted with ethyl acetate (3×30 ml). The combined organic solution was washed with water (2×50 ml), dried ($MgSO_4$), filtered and concentrated to a small volume. The concentrated solution was chromatographed on a silica gel column and eluted with methylene/petroleum ether/ethyl acetate (1:5:1) to yield the product mp: 186°–188° C.; $^1$H NMR ($CDCl_3$) δ0.90 (s, 3H, 18-$CH_3$), 6.62 (s, 1H, NH), 6.78–8.60 (m, 7H, aromatic). Analysis calculated for $C_{24}H_{26}N_2O_5S$: C 63.42; H 5.77; N 6.16. Found C 63.29; H 5.84; N 6.02.

EXAMPLE II

The synthesis of 3[(3-aminophenylsulfonyl)-amino]estra-1,3,5(10)triene-17-one was as follows:

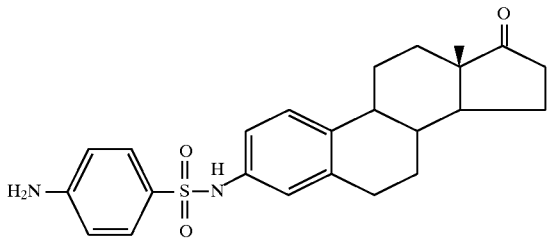

To a solution of 3[(3-nitrophenylsulfonyl)-amino] estra-1,3,5(10)-triene-17-one (0.3 g, 0.66 mmol) in 20 ml of ethanol at room temperature was added stannous chloride ($SnCl_2$) (0.74 g, 3.3 mmol). The mixture was heated to 70° C. under nitrogen and stirring continued for three hours to yield a brown solution. The solution was allowed to cool down, and poured into ice water (100 ml). The aqueous solution was made basic (pH 8) by adding saturated sodium carbonate solution. The solution was then extracted with ethyl acetate (3×40 ml). The organic layer was washed with brine (2×50 ml), dried ($MgSO_4$), filtered and concentrated. The concentrated solution was chromatographed on a silica column and eluted with methylene chloride/petroleum ether/ethyl acetate (1:5:1) to yield the product mp: 186.5–188.5 $^1$H NMR ($CDCl_3$) δ0.87 (s, 3H, 18-$CH_3$), 6.55 (s, 1H, NH), 6.78–7.24 (m, 7H, aromatic). Analysis calculated for $C_{24}H_{28}N_2O_3S$:C 67.90; H 6.65; N 6.60. Found C 67.82; H 6.72; N 6.52.

EXAMPLE III

The synthesis of 3 [(trifluoromethylcarbonyl)-amino]estra-1,3,5(10)-triene-17-one was as follows:

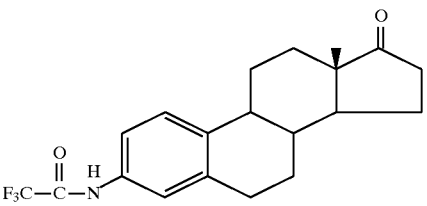

The synthesis of 3 [(trifluoromethylcarbonyl)-amino]estra-1,3,5(10)-triene-17-one is the same as the synthesis of 3 [(trifluoromethylsulfonyl)-amino] estra-1,3,5(10)-triene-17-one except the reagent trifluoromethane sulfonic anhydride was substituted with trifluoracetic anhydride. $^1$NMR ($CDCl_3$) δ0.92 (s, 3H, 18-$CH_3$), 7.28–7.36 (m, 3H, aromatic), 7.80 (s, 1H, NH). Analysis calculated for $C_{20}H_{22}F_3NO_2$:C 65.74; H 6.07; N 3.62. Found C 65.85; H 6.32; N 3.61.

EXAMPLE IV

Synthesis of 3β[{3-nitrophenylsulfonyl}-amino]pregna-5-ene-20-one could be done as follows:

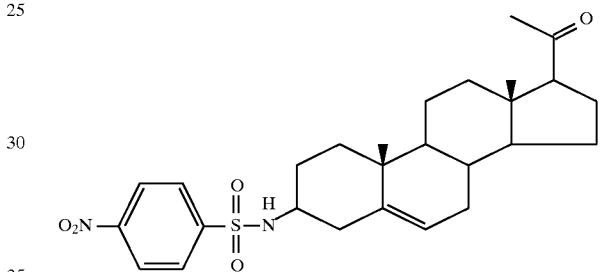

3-Nitrophenylsulfonyl chloride (1.65 g, 7.4 mmol) was added in one portion to a stirred solution of 3β-amino-pregna-5-ene-20-one (0.89 g, 3.7 mmol) in anhydrous pyridine (25 ml) at 0° C. The reaction mixture was allowed to warm to room temperature and stirring continued for 24 hours. The reaction mixture was poured onto ice and the resulting aqueous solution was extracted with ethyl acetate (3×30 ml). The combined organic solution was washed with water (2×50 ml), dried ($MgSO_4$), filtered and concentrated to a small volume. The concentrated solution was chromatographed on a silica gel column and eluted with methylene/petroleum ether/ethyl acetate (1:5:1) to yield the product.

EXAMPLE V

Synthesis of 3β[{3-nitrophenylsulfonyl}-amino] androst-5-ene-17-one could be done as follows:

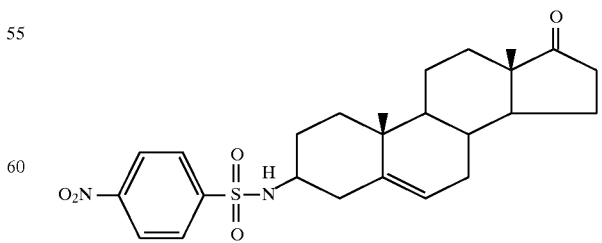

3-Nitrophenylsulfonyl chloride (1.65 g, 7.4 mmol) was added in one portion to a stirred solution of 3β-amino-androst-5-ene-17-one (1 g, 3.7 mmol) in anhydrous pyridine (25 ml) at 0° C. The reaction mixture was allowed to warm to room temperature and stirring continued for 24 hours. The reaction mixture was poured onto ice and the resulting aqueous solution was extracted with ethyl acetate (3×30 ml). The combined organic solution was washed with water (2×50 ml), dried (MgSO$_4$), filtered and concentrated to a small volume. The concentrated solution was chromatographed on a silica gel column and eluted with methylene/ petroleum ether/ethyl acetate (1:5:1) to yield the product.

EXAMPLE VI

Synthesis of 3β[{trifluoromethylsulfonyl}-amino] pregna-5-ene-20-one could be done as follows:

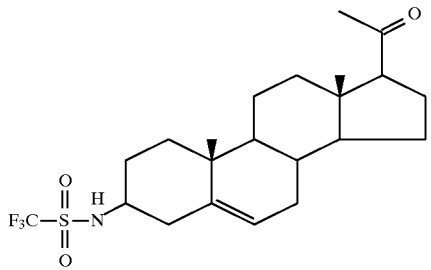

Trifluoromethane sulfonic anhydride (1.26 g, 4.46 mmol) in one portion was added to a solution of 3β-amino-pregna-5-ene-20-one (0.89 g, 3.7 mmol) and triethylamine (0.62 ml, 4.46 mmol) in dry methylene chloride (30 ml). The reaction mixture was stirred at 0° C. for one hour and the resulting mixture was washed with 10% HCl (2×50 ml), 10% NaHCO$_3$ (2×50 ml), and brine (50 ml), dried with MgSO$_4$ and concentrated to a small volume. The concentrated solution was applied to a silica gel column and eluted with methylene chloride/petroleum ether/ethyl acetate (1:3:1) to obtain the product.

EXAMPLE VII

Synthesis of 3β[{trifluoromethylsulfonyl}-amino] androst-5-ene-17-one could be done as follows:

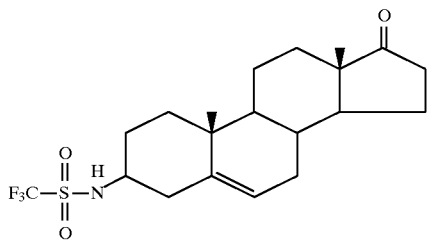

Trifluoromethane sulfonic anhydride (1.26 g, 4.46 mmol) in one portion was added to a solution of 3β-amino-androst-5-ene-17-one (1 g, 3.7 mmol) and triethylamine (0.62 ml, 4.46 mmol) in dry methylene chloride (30 ml). The reaction mixture was stirred at 0° C. for one hour and the resulting mixture was washed with 10% HCl (2×50 ml), 10% NaHCO$_3$ (2×50 ml), and brine (50 ml), dried with MgSO$_4$ and concentrated to a small volume. The concentrated solution was applied to a silica gel column and eluted with methylene chloride/petroleum ether/ethyl acetate (1:3:1) to obtain the product.

EXAMPLE VIII

Synthesis of 3β[{trifluoromethylcarbonyl}-amino] androst-5-ene-17-one could be done as follows:

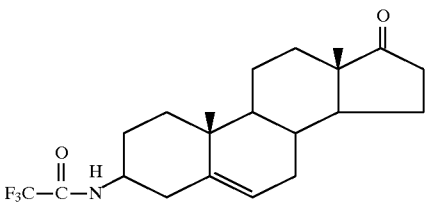

The synthesis of be 3β[{trifluoromethylcarbonyl}-amino] androst-5-ene-17-one was the same as the synthesis of 3[{trifluoromethylsulfonyl}-amino]estra-1,3,5(10)-triene-17-one except the reagent trifluoromethane sulfonic anhydride was substituted with trifluoracetic anhydride.

EXAMPLE IX

Synthesis of 3β[{trifluoromethylcarbonyl}-amino] pregna-5-ene-20-one could be done as follows:

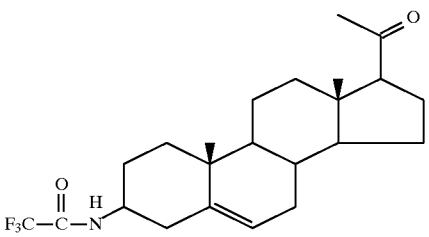

The synthesis of 3β[{trifluoromethylcarbonyl}-amino] pregna-5-ene-2-one was the same as the synthesis of 3[{trifluoromethylsulfonyl}-amino]estra- 1,3,5(10)-triene-17-one except the reagent trifluoromethane sulfonic anhydride was substituted with trifluoracetic anhydride.

EXAMPLE X

Synthesis of 3β[{3-nitrophenylsulfonyl}-amino]androst-5-ene-17-one could be done as follows:

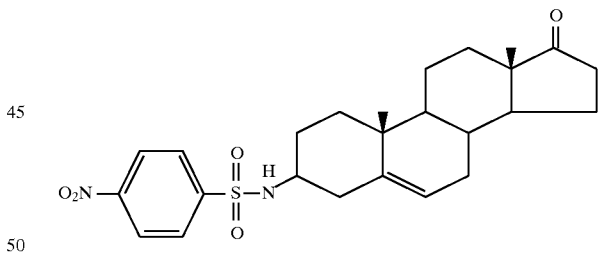

3-Nitrophenylsulfonyl chloride (1.65 g, 7.4 mmol) was added in one portion to a stirred solution of 3β-amino-androst-5-ene-17-one (1 g, 3.7 mmol) in anhydrous pyridine (25 ml) at 0° C. The reaction mixture was allowed to warm to room temperature and stirring continued for 24 hours. The reaction mixture was poured onto ice and the resulting aqueous solution was extracted with ethyl acetate (3×30 ml). The combined organic solution was washed with water (2×50 ml), dried (MgSO$_4$), filtered and concentrated to a small volume. The concentrated solution was chromatographed on a silica gel column and eluted with methylene/ petroleum ether/ethyl acetate (1:5:1) to yield the product.

EXAMPLE XI

The methods of testing the prepared compounds were as follows:

(1) Preparation of human placental microsome

Human placenta were obtained immediately upon delivery from Mercy Hospital of Pittsburgh, Pa. and stored on ice during transportation to the laboratory. The preparation of microsomes was performed according to the method of Reed and Ohno. (K. C. Reed and S. Ohno, *J. Bio. Chem.*, 251, p. 1625–31 (1976)). All procedures were carried out at 0°–4° C. The placenta was cut free of connective tissue and large blood vessels with scissors. The tissue was then homogenized in a Waring blender with two parts of tissues to one part of homogenization buffer consisting of 0.05M sodium phosphate, 0.25M sucrose, and 0.04M nicotinamide, pH 7. The homogenate was centrifuged at 10,000 g for 30 minutes. The debris was discarded and the supernatant was centrifuged at 10,5000 g for one hour. The procedure was repeated once again and the resulting pellets were stored at 70° C. The pellets were used within six weeks after preparation.

(2) Inhibitors' Screening Assay Procedure

[6,7-$^3$H] Estrone sulfate (60 $\mu$M/tube; 1 $\mu$Ci/tube) in ethanol and an inhibitor (60 or 300 $\mu$M/tube) in ethanol were added to a 5 ml test tube. The ethanol was removed with a stream of nitrogen. Tris-HCl buffer (0.05M, pH 7.2, 0.8 mL) was added to each tube. Placental microsomes were then diluted with 0.05M Tris-HCl buffer of pH 7.2 (1 mg of microsomal protein/ml of buffer). The microsomes and assay tubes containing steroids were pre-incubated for five minutes at 37° C. in a water bath shaker. The assay began by the addition of the microsomes (0.2 mL) to the tubes. After 30 minutes of incubation at 37° C., 2 mL of ethyl acetate was added to quench the assay. [$^{14}$C]Estrone (10000 dpm/tube) was added concurrently with ethyl acetate as internal standard for the determination of extraction efficiency. Control samples with no inhibitor were incubated simultaneously. Blank samples were obtained by incubating boiled microsomes. Unconjugated estrone was extracted with 3×1 mL of ethyl acetate, and the ethyl acetate layer was combined, dried (MgSO$_4$) and removed. Estrone was purified by thin-layer chromatography using methylene chloride/ether (9:1), followed by a second chromatography using toluene-ethanol (13% ethanol, vol/wt). The zone corresponding to estrone was scraped off and extracted with ethanol. Aliquots were taken for determination of radioactivity. All the samples were run three times in triplicate with variation of less than 7%. Product formation for samples containing an inhibitor was compared to that of the control samples (without inhibitors) run simultaneously. This was reported as percent inhibition of control samples which equals $$100\% \times \frac{\text{product formation for sample containing inhibitor}}{\text{product formation for sample with no inhibitor(control)}}$$

Figure 2:
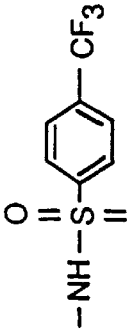
FIG. 2 discloses inhibition of estrone sulfatase activity by substituted sulfonyl-amino estra-1,3,5(10)triene-17-one in human placental microsome.

This is shown in FIGS. 1 and 2.

(3) Procedure for measuring inhibition of cell proliferation in MCF-7 cells by estrone sulfatase inhibitor. MCF-7 cell is an estrogen-dependent human breast cancer line containing estrone sulfatase activity.

Day 1. The cells were plated in MCF-7 growth media (RPMI 1640 with L-glutamine, antibiotic/antimycotic, gentamicin, 5% fetal calf serum). This allows cells to attach to the plate.

Day 2. The media was changed to steroid free media (RPMI 1640 phenol red free with L-glutamine, antibiotic/antimycotic, gentamicin, 5% fetal calf serum). The cells were maintained in the media for five days.

Day 7. To begin the experiment the cells are divided into different groups
Group 1—cells with only steroid free media
Group 2—cells with steroid free media+1 $\mu$M estradiol (used to demonstrate the cells are estrogen dependent)
Group 3—cells with steroid free media+1 $\mu$M of estrone sulfate
Group 4—cells with steroid free media+1 $\mu$M of estrone sulfate+inhibitors (10 $\mu$M)
Group 5—cells with steroid free media+inhibitors (10 $\mu$M)—this is to test the endogenous estrogenicity of the inhibitors.

At the beginning of the experiment, all the groups have the same number of cells (about 20,000) and the exact number of cells are counted.

Day 11. The media is discarded in all the groups, rinsed with PBS and the new media and steroids are added to the groups with the same concentrations as in Day 7.

Day 14. The media is discarded, the cells are rinsed with PBS and the cells counted.

All experiments were run in quadruplicate and repeated at least twice.

Antiproliferative effects of the inhibitors (group 4) were compared to that of the control samples (group 3) run simultaneously and are reported as percent inhibition of proliferation of control samples which equals $$\frac{\text{number of cells of group 4 (inhibitor)}}{\text{number of cells of group 3 (control)}} \times 100\%$$

Figure 3:
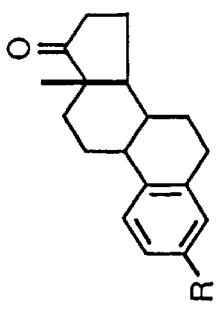
FIG. 3 discloses percent inhibition of MCF-7 breast cancer cell proliferation by estrone sulfatase inhibitors.

This is shown in FIG. 3.

(4) Estrogenicity and anti-estrogenicity procedure.

The present invention deals with using estra-1,3,5(10) triene-17-one, 3 amino derivatives and the respective dehydroepiandrosterone and pregnenolone derivatives as estrone sulfatase inhibitors. Little is known about the metabolism of these compounds and the possible effects of their metabolites in vivo. One probable metabolite of the estra 1,3,5(10) triene-17-one derivative is estra-1,3,5(10)triene-17-one, 3-amine ($E_1$-$NH_2$). The procedure and results of the estrogenicity, anti-estrogenicity and estrogen receptor binding affinity of $E_1NH_2$ are shown below.

Estrogenicity and antiestrogenicity were assessed using an ovariectomized rat uterine weight gain assay. Ovariectomized adult female rats (225–250 g) were purchased from Zivic-Miller Laboratories, Inc. (Zelienople, Pa.), and housed in the Duquesne University animal care facility. Ovariectomized rats were maintained two weeks prior to treatment to allow their uteri to regress to basal size. Treatments were given by intraperitoneal injection in a 1% gelatin, 0.9% NaCl solution at a volume of 0.5 ml. Steroids were dissolved in ethanol to 1 mg/ml then further diluted into the injection solution to the desired concentration. All treatments were continued for seven days. At the termination of the experiments, animals were sacrificed by cervical dislocation under ether anesthesia. Body weight was taken, then uteri were excised, stripped of fat, and weighed to the nearest 0.1 mg. In vivo, estradiol and estrone can induce uterine weight gain in female ovariectomized rats.

For determination of estrogenicity, four treatment groups were established: vehicle control, estradiol-17β, estrone, and estra-1,3,5(10 triene-17-one, 3 amine ($E_1$-$NH_2$). Steroids were administered at 25 $\mu$g/day. For determination of antiestrogenicity, three treatment groups were established: vehicle control, estrone, and estrone $E_1NH_2$. Estrone was administered at 2 $\mu$g/day while $E_1$-$NH_2$ was given at 100

μg/day to determine if $E_1NH_2$ could block estrone-induced uterine growth. If $E_1NH_2$ is an anti-estrogen, it would block the uterine weight gain ability of estrone.

Results for estrogenic and anti-estrogenic activity

A rat uterine weight gain assay was used to determine if $E_1$-$NH_2$ had estrogenic or anti-estrogenic activity. Estrogenicity was assessed by measuring increases in uterine weight of ovariectomized rats after treatment with the compound $E_1$-$NH_2$ did not cause a significant increase in uterine weight over with estrogen when given at 25 μg/day for seven days. In contrast, both estradiol and estrone significantly increased uterine weight above control levels (no estrogen). This is shown in figure IV where ovariectomized rats were treated for seven days with 25 μg/day of estradiol, estrone, $E_1$-$NH_2$. Data are mean ±SEM, n=5 for all groups. Control animals received vehicle only (0.9% NaCl, 1% gelatin, 500 μl, i.p. injection). A statistical analysis of variants (ANOVA) indicated significant differences between groups (F=54.77, 4, 20 df, $P \leq 0.001$). Uterine weights of rats from estrone and estradiol groups were significantly ($p \leq 0.05$) higher than other groups (control and $E_1$-$NH_2$) as determined by Student-Newman-Keuls test. Uterine weight of $E_1$-$NH_2$ is not significantly different from the control group.

Figure 5:
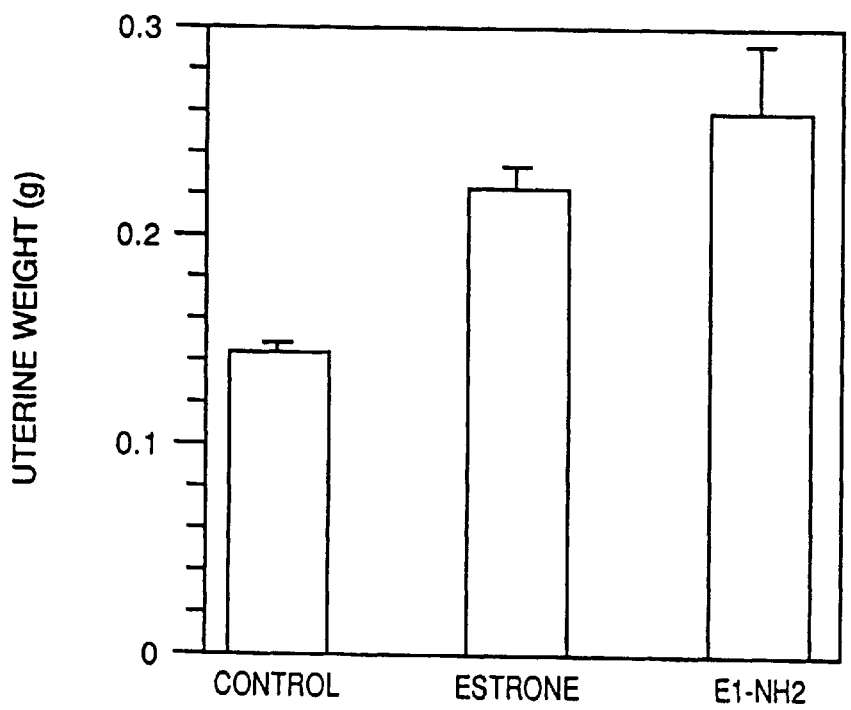
FIG. 5 discloses the anti-estrogenicity of $E_1$-$NH_2$ as determined by rat uterine weight gain assay.

Antiestrogenicity was assessed as the ability of the compound to block estrone-induced uterine weight gain in ovariectomized rats. When $E_1$-$NH_2$ (100 μg/day) was given simultaneously with estrone (2 μg/day), there was a significant increase in uterine weight compared with control vehicle. The increase in uterine weight for $E_1$-$NH_2$+estrone was of the same magnitude as the increase observed for the estrone-only treatment group, indicating that the compound $E_1NH_2$ did not block estrone-induced uterine growth. This is shown by FIG. 5 where data are means ±SEM, n=5 for all groups. Ovariectomized rats were treated for seven days with 100 μg/day of $E_1$-$NH_2$ in combination with 2 μg/day. Control animals received vehicle only (0.9% NaCl, 1% gelatin, 500 μl, i.p. injection). ANOVA indicated significant differences between groups (F=6.71,3,16 df, $P \leq 0.005$). Uterine weights of rats from $E_1$-$NH_2$ group was not significantly different from the estrone group.

(5) Estrogen receptor binding.

To further test whether $E_1NH_2$ had estrogenic or antiestrogenic activity is to determine its ability to bind to estrogen receptors. Estrogen receptor binding was measured using an $^3$H-estradiol binding assay of rat uterine cytosol. Uteri were weighed, minced with scissors, then homogenized in TEMG buffer with a Tissue Tearor homogenizer (Biospec Products, Bartlesville, Okla.) using three bursts of 30 sec each. The homogenate was centrifuged at 1,000×g for 10 min at 4° C., after which the supernatant was decanted. Supernatant from the low-speed nuclear centrifugation was transferred to polyallomer tubes and centrifuged at 170.000×g for 1 h at 4° C. The resulting supernatant was diluted 1:1 (vol:vol) with TEMG buffer, and this constituted the cytosol preparation.

Aliquots (300 μl) of cytosol were incubated in a total volume of 500 μl with 1 nM of $^3$H-estradiol for determination of total binding. A parallel set of samples was incubated with 1 μM radio-inert estradiol for determination of nonspecific binding. Specific binding was calculated as total binding minus nonspecific binding. Another parallel set of samples was incubated with varying concentrations (1, 0.1 and 0.01 μM) of competitors. Samples were incubated for 16– 20 h at 4° C. After incubation of cytosol samples, free steroid was removed by addition of 500 μl of dextran-coated charcoal for 3 min. followed by centrifugation at 1,500×g for 3 min. The supernatant was decanted into scintillation vials and four ml of scintillation cocktail was added. Samples were counted in a Packard Tri-carb liquid scintillation spectrometer at 50% efficiency. Data for binding in the presence of competitors is expressed as a percentage of specific binding.

Figure 6:
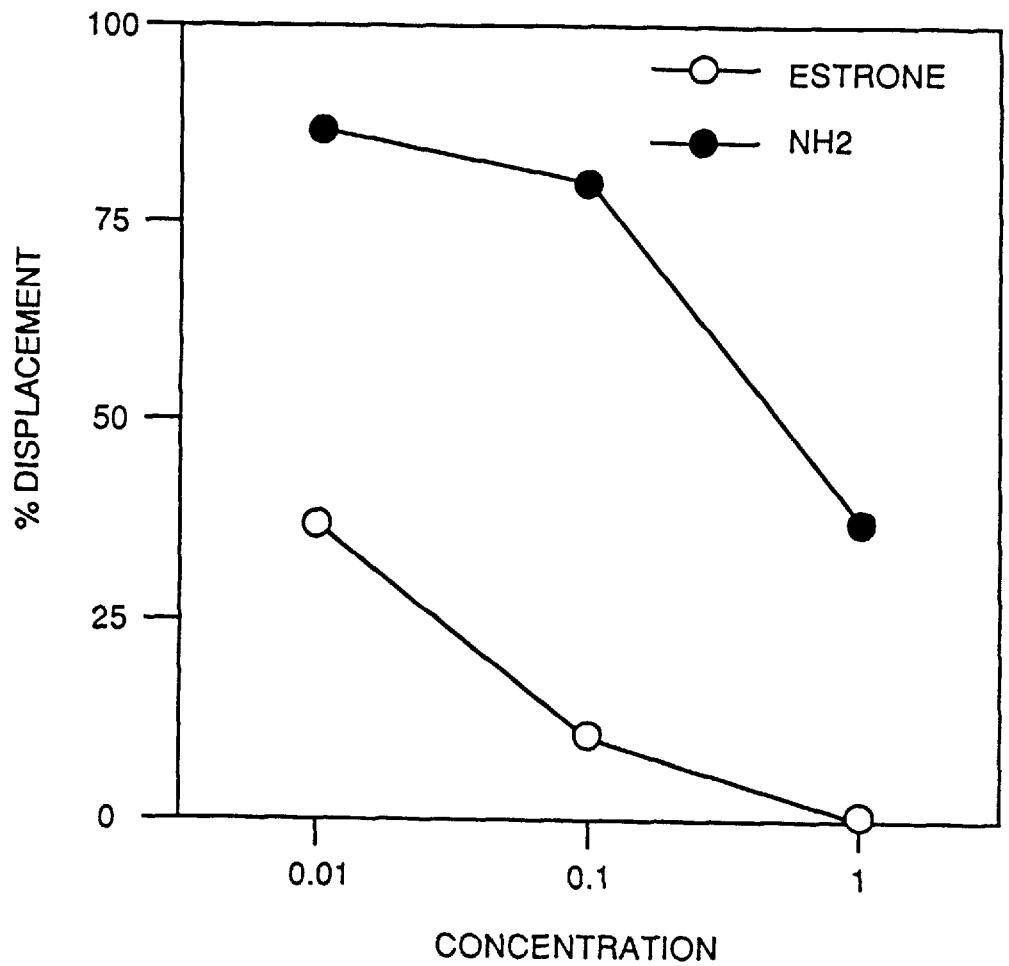
FIG. 6 discloses the displacement of specific $^3H$-estradiol binding to the rat uterine estrogen receptor.

The ability of $E_1$-$NH_2$ to bind to the estrogen receptor was determined using a $^2$H-estradiol binding assay. FIG. 6 shows the percentage of specific $^3$H-estradiol binding in the presence of the test compound at three concentrations. $E_1$-$NH_2$ did not compete for estrogen receptor at the same level as estrone, which displaced 100% of the specific $^3$H-estradiol binding at a 1000-fold excess. $E_1$-$NH_2$ displaced 60% of $^3$H-estradiol binding at 1000-fold excess. This is shown by FIG. 6 wherein rat uterine cytosol was used as a source of estrogen receptor. $^3$H-estradiol was added at nM and competitor ($E_1$-$NH_2$) was added at 0.01, 0.1, and 1 μM. Data are expressed as a percentage of specific binding (total binding minus binding in the presence of 1 1 μM radio-inert estradiol).

CONCLUSION

Little is known of the in vivo metabolism of the test inhibitors (estra-1,3,5(10)-17-one, 3-amine derivatives). A potential primary metabolite of the test inhibitor was estra-1,3,5(10)-17-one, 3-amine ($E_1$-$NH_2$). An in vivo approach was used (ovariectomized rat uterine weight gain assay) to test for estrogenicity and anti-estrogenicity of $E_1$-$NH_2$. The ovariectomized rat uterine weight gain assay was a sensitive and reliable method of assessing the ability of a compound to elicit estrogen-dependent actions under physiological conditions.

Figure 4:
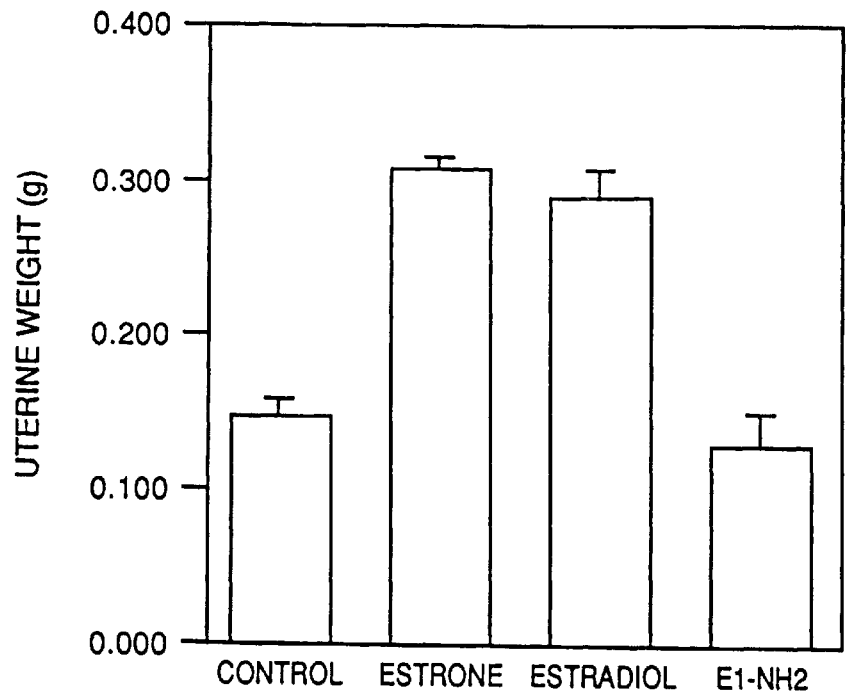
FIG. 4 discloses estrogenicity of estra-1,3,5(10)-triene-17-one, 3 amine ($E_1$-$NH_2$) as determined by rat uterine weight gain assay.

$E_1$-$NH_2$ is neither estrogenic nor anti-estrogenic (FIGS. 4 and 5). This is an important finding since it would be disadvantageous for an estrone sulfatase inhibitor used in the treatment of estrogen-dependent cancer to be metabolized to a compound that was estrogenic. Furthermore, $E_1$-$NH_2$ does not interact to any great extent with an estrogen receptor (FIG. 6). These properties taken together indicate that $E_1$-$NH_2$ would not cause significant problem if it were the primary metabolite of an estrone sulfatase inhibitors of the present invention used for the treatment of estrogen-dependent illnesses.

Several newly synthesized estra-1,3,5(10)-17-one, 3-amine derivatives inhibited estrone sulfatase activity of human placental microsomes. The degree of inhibition varied among the different derivatives. In addition, the test compounds also inhibited proliferation of estrone sulfatase containing estrogen-dependent MCF-7 cells when cells were grown with estrone sulfate as their sole source of estrogen. The data indicated that estra-1,3,5(10)-17-one, 3 amine derivatives are useful as therapeutic and prophylactic agents for estrogen-dependent illnesses.

Whereas particular embodiments of this invention have been described above for the purposes of illustration, it will be evident to those skilled in the art that numerous variations of the details of the present invention may be made without departing from the invention as described in the appended claims.

We claim:
1. A compound comprising the formula (1)

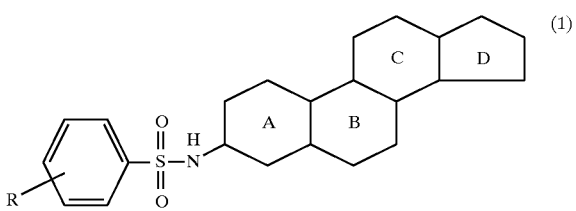

wherein (a) R is selected from the group consisting of hydrogen, a lower alkyl group, an alkoxy group, halogen, NH$_2$, NO$_2$, C≡N, and N=C=S and (b) the ring system ABCD is a steroid nucleus selected from the group consisting of estrone, dehydroepiandrosterone, estradiols, estradiolesters, pregnenolone, substituted estrones, substituted dehydroepiandrosterones, substituted estradiols, substituted estradiolesters and substituted pregnenolone.

2. The compound of claim 1, wherein said lower alkyl group has one to six carbon atoms, wherein said alkoxy group has one to four carbon atoms and wherein said halogen is selected from the group consisting of fluorine, chlorine, bromine and iodine.

3. The compounds of claim 1 comprising the species formula (2)

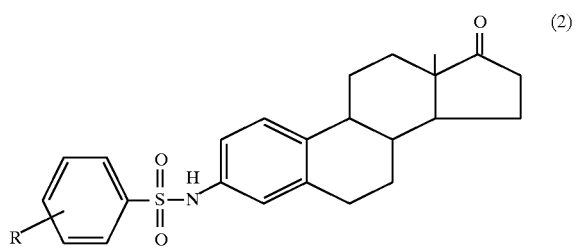

wherein R is selected from the group consisting of hydrogen, a lower alkyl group of one to six carbon atoms, an alkoxy group of one to four carbon atoms, NH$_2$, NO$_2$, C≡N, N=C=S and a halogen selected from the group consisting of F, Cl, Br and I.

4. The compound of claim 3 wherein R is hydrogen.
5. The compound of claim 3 wherein R is 4-methyl.
6. The compound of claim 3 wherein R is 4-methoxy.
7. The compound of claim 3 wherein R is a nitro selected from the group consisting of 2-NO$_2$, 3-NO$_2$ and 4-NO$_2$.
8. The compound of claim 3 wherein R is a halogen selected from the group consisting of 4-fluoro, 4-chloro, 4-bromo, 4-iodo.
9. The compound of claim 3 wherein R is selected from the group consisting of 2-NH$_2$ and 3-NH$_2$ and 4-NH$_2$.

10. The compounds of claim 1 comprising the species formula (3)

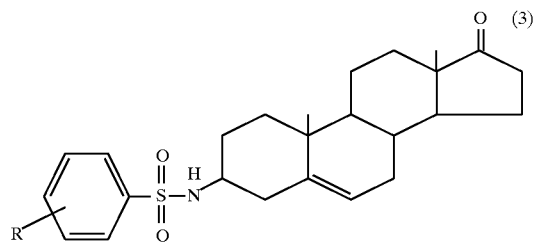

wherein R is selected from the group consisting of hydrogen, a lower alkyl group of one to six carbon atoms, an alkoxy group of one to four carbon atoms, NH$_2$, NO$_2$, C≡N, N=C=S and a halogen selected from the group consisting of F, Cl, Br and I.

11. The compound of claim 10 wherein R is Hydrogen.
12. The compound of claim 10 wherein R is 4-methoxy.
13. The compound of claim 10 wherein R is a nitro selected from the group consisting of 2-NO$_2$, 3-NO$_2$ and 4-NO$_2$.
14. The compound of claim 10 wherein R is a halogen selected from the group consisting of 4-fluoro, 4-chloro, 4-bromo, 4-iodo.
15. The compound of claim 10 wherein R is selected from the group consisting of 2-NH$_2$ and 3-NH$_2$ and 4-NH$_2$.

16. The compounds of claim 1 comprising the species formula (4)

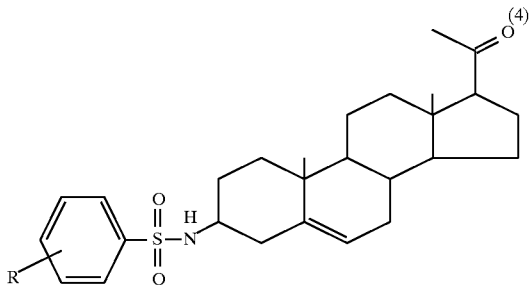

wherein R is selected from the group consisting of hydrogen, a lower alkyl group of one to six carbon atoms, an alkoxy group of one to four carbon atoms, NH$_2$, NO$_2$, C≡N, N=C=S and a halogen selected from the group consisting of F, Cl, Br and I.

17. The compound of claim 16 wherein R is hydrogen.
18. The compound of claim 16 wherein R is 4-methoxy.
19. The compound of claim 16 wherein R is a nitro selected from the group consisting of 2-NO$_2$, 3-NO$_2$ and 4-NO$_2$.
20. The compound of claim 16 wherein R is a halogen selected from the group consisting of 4-fluoro, 4-chloro, 4-bromo, 4-iodo.
21. The compound of claim 16 wherein R is selected from the group consisting of 2-NH$_2$, 3-NH$_2$ and 4-NH$_2$.

22. A method of therapeutically treating a patient comprising providing a compound having the formula (1)

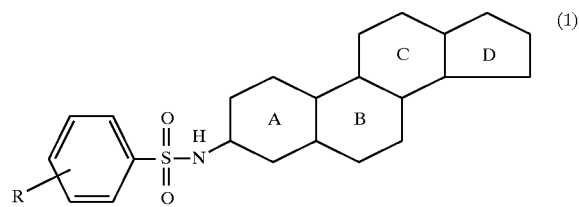

wherein R is selected from the group consisting of hydrogen, a lower alkyl group, an alkoxy, halogen, NH$_2$, NO$_2$, C≡N and N=C=S and the ring system ABCD is a steroid nucleus selected from the group consisting of estrone, dehydroepiandrosterone, estradiols, estradiolesters, pregnenolone, substituted estrones, substituted dehydroepiandrosterones, substituted estradiols, substituted estradiolesters and substituted pregnenolone,
  incorporating said compound in a suitable pharmaceutical carrier;
  administering a therapeutically effective dosage of said compound incorporated in said carrier to said patient; and
  employing said method in therapeutically treating a patient for estrogen related diseases selected from the group consisting of breast cancer, ovarian cancer, vaginal cancer, endometrial cancer and endometriosis.

23. The method of claim 22, including employing as said carrier a solution selected from the group consisting of physiologic saline and 5% dextrose.

24. The method of claim 23, including administering said compound incorporated in said carrier to a patient by the parenteral route.

25. The method of claim 23, including administering said compound incorporated in said carrier to a patient by the oral route.

26. The method of therapeutically treating a patient of claim 22 employing a compound having the species formula (2)

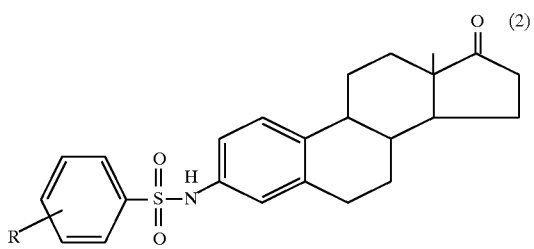

wherein R is selected from the group consisting of hydrogen, a lower alkyl group of one to six carbon atoms, a alkoxy group of one to four carbon atoms, $NH_2$, $NO_2$, $C\equiv N$, $N=C=S$ and a halogen selected from the group consisting of F, Cl, Br and I.

27. The method of claim 26, including employing as said carrier a solution selected from the group consisting of physiologic saline and 5% dextrose in water.

28. The method of claim 27, including administering said compound by injection into a patient.

29. The method of claim 27, including administering said compound incorporated in said carrier to a patient by the parenteral route.

30. The method of claim 27, including administering said compound incorporated in said carrier to a patient by the oral route.

31. The method of therapeutically treating a patient of claim 22 employing a compound having the species formula (3)

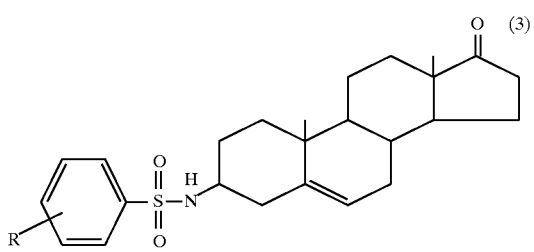

wherein R is selected from the group consisting of hydrogen, a lower alkyl group of one to six carbon atoms, an alkoxy group of one to four carbon atoms, $NH_2$, $NO_2$, $C\equiv N$, $N=C=S$ and a halogen selected from the group consisting of F, Cl, Br and I.

32. The method of claim 31, including employing as sad carrier a solution selected from the group consisting of physiologic saline and 5% dextrose in water.

33. The method of claim 32, including administering said compound to a patient by injection.

34. The method of claim 32, including employing said carrier to said patient by the parenteral route.

35. The method of claim 32, including administering said compound incorporated in said carrier to said patient by the oral route.

36. The method of therapeutically treating a patient of claim 22 employing a compound having the species formula (4)

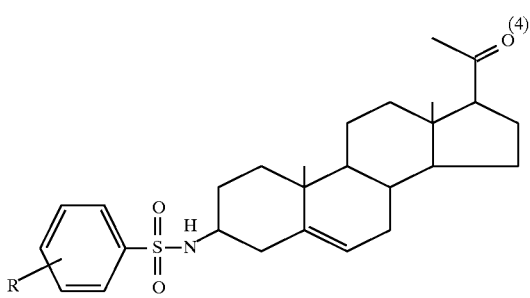

wherein R is selected from the group consisting of hydrogen, a lower alkyl group of one to six carbon atoms, an alkoxy group of one to four carbon atoms, $NH_2$, $NO_2$, $C\equiv N$, $N=C=S$ and a halogen selected from the group consisting of F, Cl, Br and I.

37. The method of claim 36, including employing said carrier a solution selected from the group consisting of physiologic saline and 5% dextrose in water.

38. The method of claim 37, including administrating said compound in said carrier by injection.

39. The method of claim 37, including employing said carrier to a patient by the parenteral route.

40. The method of claim 37, including administering said compound incorporated in said carrier to a patient by the oral route.

* * * * *

UNITED STATES PATENT AND TRADEMARK OFFICE
CERTIFICATE OF CORRECTION

PATENT NO. : 5,866,603

DATED : February 2, 1999

INVENTOR(S) : Li et al.

It is certified that error appears in the above-identified patent and that said Letters Patent is hereby corrected as shown below:

Column 12, line 15, change "$^1$NMR" to -- $^1$H NMR --.

Col. 22: Claim 32, line 5, change "sad" to -- said --.

Claim 37, line 41, after "employing" insert -- as --.

Claim 38, line 45, change "administrating" to -- administering --.

Signed and Sealed this

Thirtieth Day of November, 1999

Attest:

Q. TODD DICKINSON

*Attesting Officer*  *Acting Commissioner of Patents and Trademarks*